(12) United States Patent
Brandl et al.

(10) Patent No.: US 8,114,061 B2
(45) Date of Patent: Feb. 14, 2012

(54) WELDING SHUTTLE FOR A BAG

(75) Inventors: Matthias Brandl, Bad Koenigshofen (DE); Peter Hilgers, Schonungen (DE); Franz Kugelmann, St. Wendel/Bliesen (DE); Matthias Meisinger, Spiesen/Elversberg (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 1249 days.

(21) Appl. No.: 10/499,811

(22) PCT Filed: Apr. 16, 2002

(86) PCT No.: PCT/EP02/04221
§ 371 (c)(1),
(2), (4) Date: Jun. 30, 2004

(87) PCT Pub. No.: WO03/059241
PCT Pub. Date: Jul. 24, 2003

(65) Prior Publication Data
US 2005/0096625 A1    May 5, 2005

(30) Foreign Application Priority Data
Jan. 17, 2002    (DE) .............................. 202 00 689 U

(51) Int. Cl.
*A61B 19/00*    (2006.01)

(52) U.S. Cl. ........ 604/408; 604/403; 604/407; 604/409; 604/410; 604/411; 604/412; 604/413; 604/414; 604/415; 604/262; 604/905; 206/438; 206/484; 206/486; 206/828

(58) Field of Classification Search ........... 604/407–415
See application file for complete search history.

(56) References Cited

U.S. PATENT DOCUMENTS

| | | | |
|---|---|---|---|
| 4,516,977 A | 5/1985 | Herbert | |
| 5,823,383 A | 10/1998 | Hins | |
| 6,572,268 B2 | 6/2003 | Ichikawa | |
| 7,223,262 B2 * | 5/2007 | Brehm et al. | ................ 604/415 |
| 2003/0075469 A1 | 4/2003 | Herbert | |
| 2003/0135193 A1 | 7/2003 | Hilgers et al. | |

FOREIGN PATENT DOCUMENTS

| | | | |
|---|---|---|---|
| DE | 33 05 365 | | 9/1984 |
| DE | 38 03 776 | | 8/1989 |
| DE | 196 34 944 | | 5/1998 |
| DE | 19634944 | * | 5/1998 |
| DE | 19958952 | * | 12/1999 |
| DE | 19958952 A1 | * | 12/1999 |
| DE | 199 59 230 | | 4/2001 |
| DE | 199 58 952 | | 6/2001 |
| DE | 199 58 952 A1 | | 6/2001 |
| JP | 59 209352 A | | 11/1984 |
| JP | 9 104451 A | | 4/1997 |

(Continued)

*Primary Examiner* — Tatyana Zalukaeva
*Assistant Examiner* — Ilya Treyger
(74) *Attorney, Agent, or Firm* — Jacobson Holman PLLC

(57) ABSTRACT

A welding boat for a pouch has a center part and two prolongations extending therefrom in opposite directions and tapering acutely. The welding boat has an opening for the filling of the pouch with a substance in manufacture and inlets and outlets for the actual use of the pouch. The center part is substantially filled by an opening with a lumen which is as large as possible and preferably circular, and the side edges of the side prolongations contact the opening tangentially.

12 Claims, 2 Drawing Sheets

FOREIGN PATENT DOCUMENTS

| | | |
|---|---|---|
| JP | 11 01248 A | 1/1999 |
| JP | 11-029163 | 2/1999 |
| JP | 11 171215 A | 6/1999 |
| JP | 2000 007033 A | 1/2000 |
| JP | 2001 309964 A | 11/2001 |
| WO | WO 01/41698 A2 | 6/2001 |

* cited by examiner

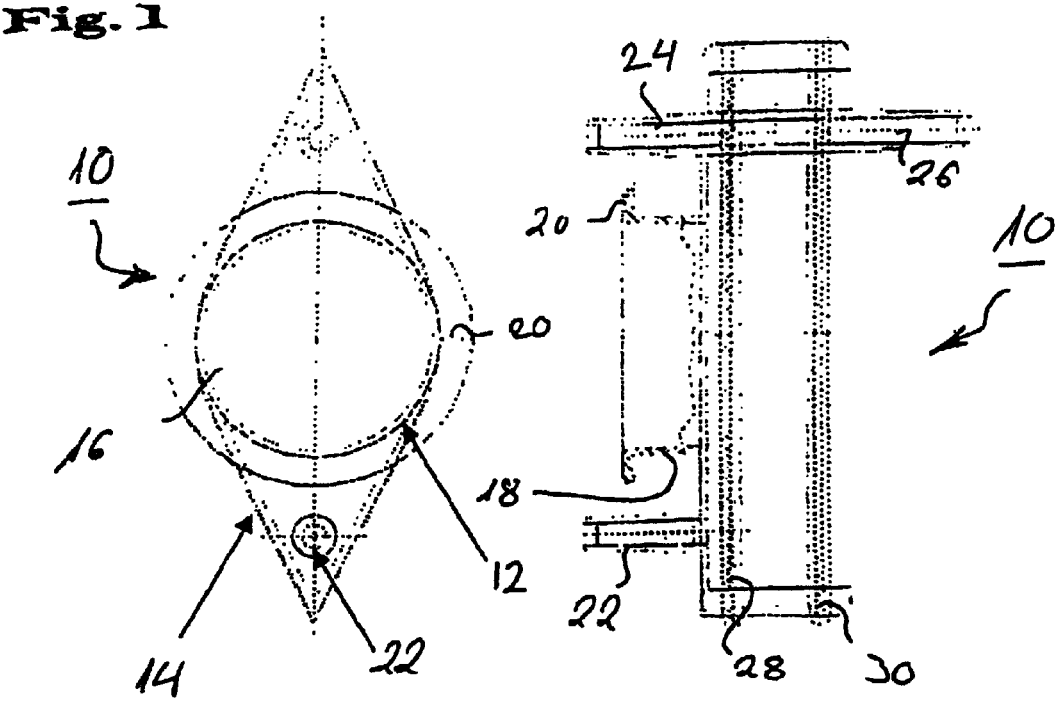
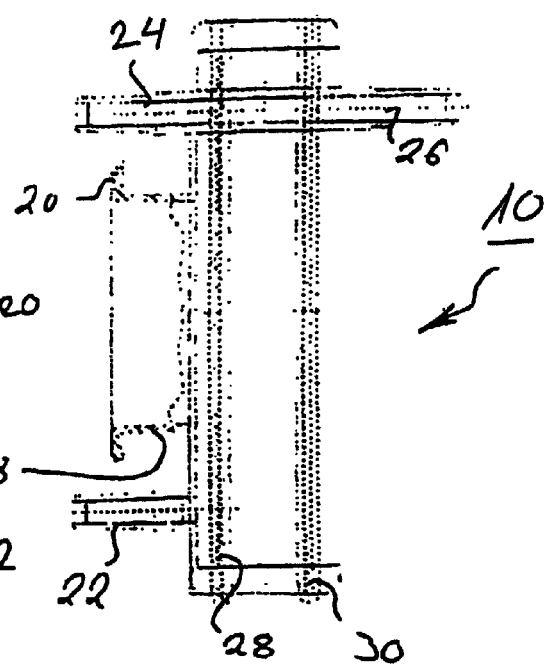
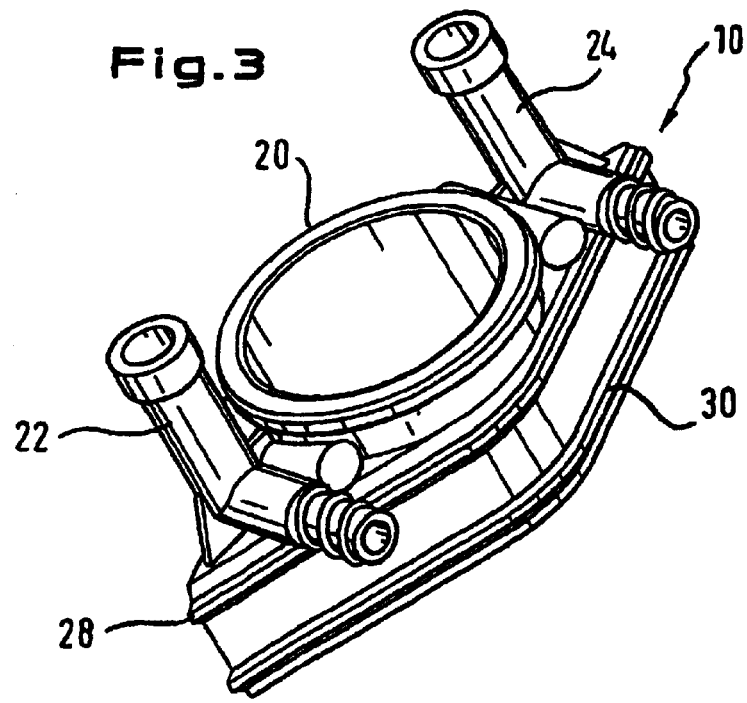

WELDING SHUTTLE FOR A BAG

CROSS-REFERENCE TO RELATED APPLICATION

This is a nationalization of PCT/EP02/04221 filed Apr. 16, 2002 and published in German.

BACKGROUND OF THE INVENTION

1. Field of Invention

The invention relates to a welding boat for a pouch.

A storage pouch is already known from DE 201 08 911 comprising a port system consisting of a welding boat for removal and introduction. A valve system is present at the pouch side here which is opened on connection with the removal or introduction part and which closes automatically on separation. The ports are formed as a Luer cone there.

2. Description of the Prior Art

A storage pouch is also known from DE 33 05 365 comprising a welding boat which has a center part and two prolongations extending in opposite directions and tapering acutely. It already has an opening at the center for the filling of the pouch with a substance on manufacture and, on the other hand, inlets and outlets for the actual use of the pouch. In the known storage pouches, the single opening is, however, only made with a very narrow lumen, whereby the filling is made difficult.

SUMMARY OF THE INVENTION

It is the object of the invention to provide a pouch with a welding boat, with the manufacturing process of the pouch being simplified and the handling by the user simultaneously being facilitated.

This object is solved in accordance with the invention in that a generic welding boat additionally has the features of the invention described herein. The center part is accordingly substantially filled by a preferably circular opening with a lumen which is as large as possible, with the side edges of the side prolongations contacting the opening tangentially. A welding boat for flexible containers such as pouches is thus created with a space-optimized arrangement which permits a simplified filling of the pouch. The connection port, i.e. the opening to fill the pouch, is characterized by a central opening with a stable shape via which the pouch as such can be filled very easily, and in particular very fast, and can subsequently be closed. Space is available due to a symmetrical geometry of the welding boat, namely the prolongations laterally contacting the opening tangentially, for further functional components such as the introduction and removal port or any evacuation ports to be connected next to the central opening for the filling of the pouch.

Advantageous embodiments of the invention result from the dependent claims following the main claim.

Accordingly, in accordance with a preferred aspect, a nose is formed, preferably molded, to the large-lumen opening of the welding boat. The pouch provided with the welding boat can be simply fixed via this nose during filling. The welding boat further developed in this matter is thus in particular suitable for use in an automatic production line for the filling of the pouches provided with the welding boat.

The ports or connectors can advantageously be arranged as required in the region of the welding boat, for example an introduction port on the one side and a removal port on the other side.

So-called weld edges are particularly advantageously provided at the periphery of the welding boat. The flexible pouch can be connected in a simpler manner along these edges via a weld connection in a closed-material connection with the welding boat. These weld edges can also only be provided for tolerance acceptance, whereas otherwise the weld is carried out over the whole side area.

Protection is additionally claimed for a pouch in accordance with the invention which contains a preferably powdery concentrate for a dialysis fluid or of parts thereof for kidney replacement treatment and which has a welding boat in accordance with the aforesaid claims.

In a preferred aspect, this pouch can have a welding boat which contains two ports. One port in this process can in particular open into the pouch via a tube as an inflow opening; the other can in particular open into the pouch as an outflow opening. Both ports are advantageously designed projecting outwardly. Devices can be located at the ends of the ports for the accommodation of functional components such as filters or hoses. It is also possible to guide a port via a tube and/or hose down to the lowest point of the pouch in order to have direct access to this region—whether for introduction or removal purposes.

BRIEF DESCRIPTION OF THE DRAWINGS

Further details and advantages will be explained with reference to an embodiment shown in the drawing. There are shown:

FIG. 1: a plan view of a welding boat in accordance with an embodiment of the present invention;

FIG. 2: a sectioned side view of the welding boat in accordance with FIG. 1;

FIG. 3: a perspective view of the welding boat which substantially corresponds to the views in accordance with FIG. 1 or FIG. 2.

DETAILED DESCRIPTION OF THE PREFERRED EMBODIMENTS

Figure 4:
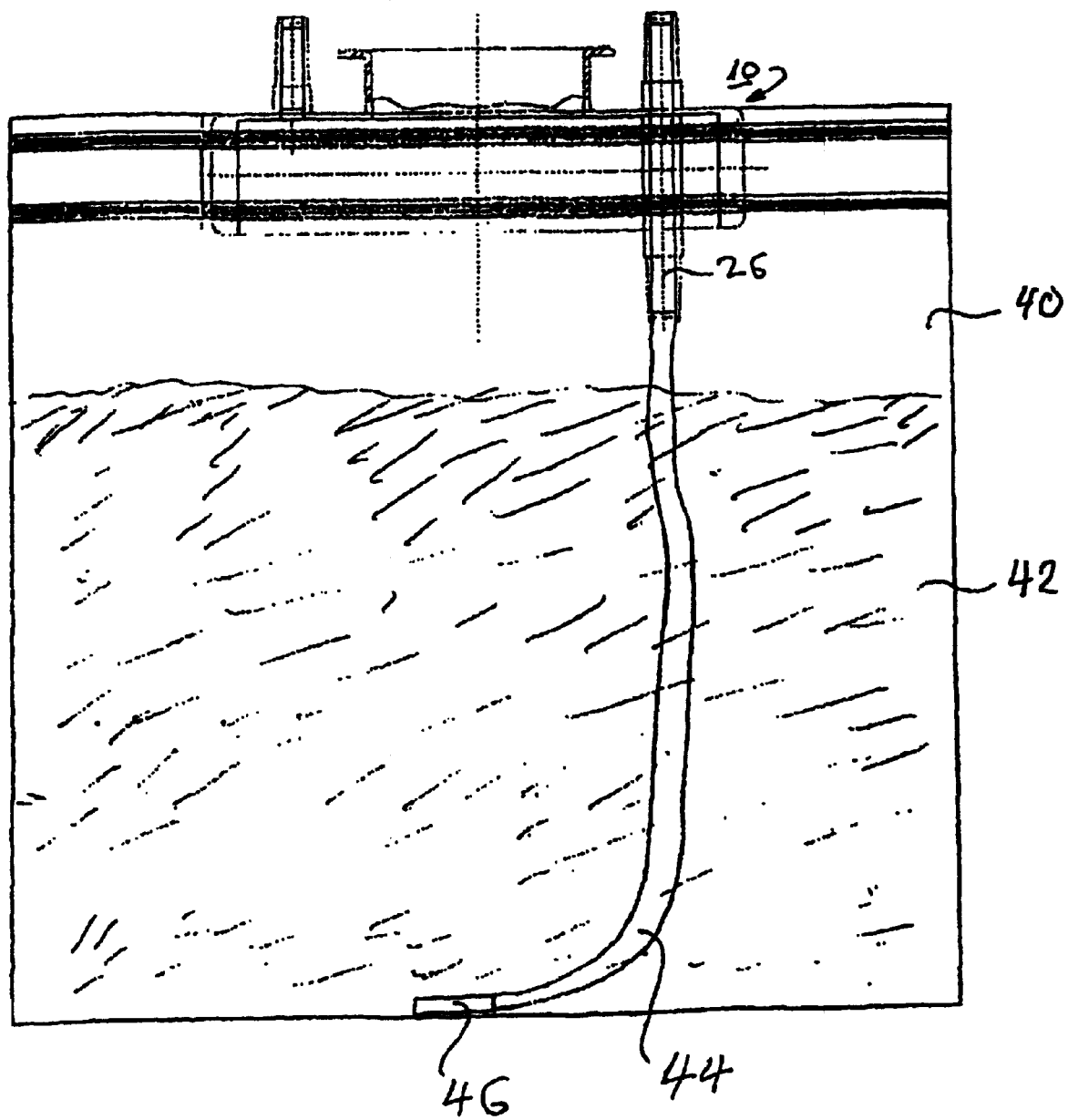
FIG. 4: a sectioned side view of a pouch having a welding boat in accordance with the invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

In the embodiment of the invention shown in the Figures, the basic design of a welding boat is described which is used, for example, for a concentrate pouch for the preparation of dialysis fluid.

The welding boat 10 consists of a center part 12 and of prolongations 14 extending in opposite directions and tapering acutely and made symmetrically to one another. As can in particular be recognized from FIG. 1, the center part 12 is substantially filled by a large lumen opening 16 which has a diameter of 35 mm in the embodiment and is circular in the present embodiment. This filling opening permits a fast and simple filling of concentrate powder. As becomes clear from FIGS. 1 and 3, the side edges of the side prolongations extend such that they contact the side wall of the opening 16 tangentially. A space optimization is hereby ensured while achieving a large lumen opening 16 for filling.

It becomes clear from FIGS. 2 and 3 that a nose 18 is molded to the opening 16 and a flange 20 is formed at its free end. This nose, on the one hand, facilitates the positioning of a filling tube (not shown in more detail here) of a filling machine. On the other hand, the opening 16 can be closed in a simple manner by pushing on or welding on a cover or a foil.

Ports 22 and 24 are arranged in the region of the prolongations 14. These connection ports 22 and 24 can be connected, for example, in a manner not shown here in more detail, directly to a water circuit. Whereas the port 22 only projects outwardly here on the welding boat 10, there is provided at the connection port 24, which also projects outwardly on the one side, a tube 26 which projects inwardly into the pouch and which can permit the connection of an inwardly projecting hose. Such a hose can, however, also be attached directly to the port.

Weld edges 28 and 30 are provided at the edge of the welding boat which ensure a simplified welding of the pouch to the welding boat.

A welding boat in accordance with FIGS. 1 to 3 serves in the embodiment shown here as the welding boat of a concentrate pouch not shown in more detail here, i.e. of a pouch which is connected to a water circuit in the preparation of a dialysis fluid in a corresponding dialysis machine. To simplify this for the user and simultaneously to prevent the intrusion of bacteria, the connection ports 22 and 24 are provided which are designed appropriately for this purpose. An opening and/or pouring of the pouch into a container integrated into the dialysis machine is thus not necessary.

For the simplification and automation of the manufacturing process, in particular the nose 18 provides an opening adapted to the filling system which in the embodiment shown here comprises approximately 35 mm. This opening can be closed after filling by a closure, for example a foil or a hard cover. The nose 18 can serve for the fixing of the pouch in the automatic production line during the total manufacturing process. Further components can also be provided at the welding boat for fixing during filling and/or use.

The design of the welding boat in accordance with the invention with a filling opening 16 which is as large as possible with a simultaneously optimized use of space of the prolongations 14 for the actual application ports is in particular advantageous on filling with powdery products, since they, in contrast to liquids, can block too narrow a filling opening more easily.

The pouch can advantageously be completely produced before filling.

After filling, the pouch volume can be minimized by evacuation of the pouch via the welding boat, whereby the concentrate powder is fixed, for example. The application of the vacuum can take place by connection of the vacuum pump to one of the ports present, by a separate port or a port in the closure of a present port.

A welding boat 10 is shown in FIG. 4 welded to a pouch 40. The pouch 40 is filled with powder 42 which serves, for example, as a concentrate for the manufacture of a dialysis fluid. The port projecting into the pouch in the form of a tube 26 supports a hose 44 to obtain access to the lowest point of the pouch. In the embodiment shown here, it is a removal port so that the hose is expediently provided with a filter element 46 at its free end to prevent solids from penetrating into the hose 44 during the picking up of a saturated fluid at the bottom of the pouch. A corresponding embodiment of the pouch could naturally also serve to allow fluid at the bottom of the pouch to flow in. A filter element 46 is not necessarily required in such a variant.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. A welding boat for a pouch, comprising:
    a center part having a central opening that includes a side wall configured as a lumen for filling of the pouch with a substance in manufacture;
    a first and a second prolongation extending in opposite directions from the center part and having side edges that respectively contact the side wall of the central opening tangentially so that the central opening substantially fills the center part within the tangential contacts, the first and the second prolongations each tapering progressively and acutely from the tangential contacts with the side wall of the central opening to a point terminus, the first and the second prolongations thereby each forming a respective tapered portion; and
    at least one inlet and at least one outlet configured for use with the pouch, the at least one inlet being located in the tapered portion of the first prolongation and the at least one outlet being located in the tapered portion of the second prolongation.

2. The welding boat in accordance with claim 1, wherein the lumen opening includes a nose.

3. The welding boat in accordance with claim 1, wherein the inlet and the outlet are configured as at least one of ports and connectors.

4. The welding boat in accordance with claim 1, wherein at least one weld edge is provided at a periphery of the boat.

5. The welding boat in accordance with claim 3, wherein an inlet port is arranged in the first prolongation and a removal port is arranged in the second prolongation.

6. An assembly of a pouch containing a concentrate and a welding boat, comprising:
    a welding boat center part having a central opening that includes a side wall configured as a lumen for filling of the pouch;
    a first and a second prolongation extending in opposite directions from the center part and having side edges that respectively contact the side wall of the central opening tangentially so that the central opening substantially fills the center part within the tangential contacts, the first and the second prolongations each tapering progressively and acutely from the tangential contacts with the side wall of the central opening to a terminus, the first and the second prolongations thereby each forming a respective tapered portion; and
    at least one inlet and at least one outlet configured for use with the pouch, the at least one inlet being located in the tapered portion of the first prolongation and the at least one outlet being located in the tapered portion of the second prolongation.

7. The assembly in accordance with claim 6, wherein the welding boat has one tubular port that projects outwardly therefrom, and another tubular port that projects outwardly therefrom and into the pouch.

8. The welding boat according to claim 1, wherein the lumen is circular.

9. The welding boat according to claim 2, wherein the nose is of molded construction.

10. The assembly according to claim 7, wherein the concentrate is a powder for a dialysis fluid.

11. A welding boat for a pouch, comprising:
a center part having a central opening that includes a side wall configured as a lumen for filling of the pouch with a substance;
a first and a second substantially V-shaped prolongation extending in opposite directions from the center part, each of the prolongations having substantially straight opposed side edges that respectively contact the side wall of the central opening tangentially so that the central opening substantially fills the center part within the tangential contacts, and each of the first and the second prolongations each tapering progressively and acutely from the tangential contacts with the side wall to a terminus, the first and the second prolongations thereby each forming a respective tapered portion; and
an inlet and an outlet configured for use with the pouch, the inlet being located in the tapered portion of the first prolongation and the outlet being located in the tapered portion of the second prolongation.

12. The welding boat according to claim 11, wherein the first and the second prolongation each include a tubular port that projects outwardly therefrom, and at least one of the first and the second prolongation includes a tubular port that projects outwardly therefrom and into the pouch.

* * * * *